United States Patent [19]

Segovia-Cortes

[11] Patent Number: 5,860,915
[45] Date of Patent: Jan. 19, 1999

[54] LAPAROSCOPIC ELEVATOR TO SIMULTANEOUSLY LIFT THE FOUR QUADRANTS OF AN ABDOMINAL CAVITY FOR LAPAROSCOPIC SURGERY

[76] Inventor: Enrique-Gerardo Segovia-Cortes, Av. Ricardo Margain Zozaya 333, Col. Sta Engracia, Garza Garcia, N. L. México, C.P., Mexico, 66267

[21] Appl. No.: 654,915

[22] Filed: May 29, 1996

[30] Foreign Application Priority Data

Dec. 11, 1995 [MX] Mexico ..................................... 955158

[51] Int. Cl.⁶ ....................................................... A61B 1/22
[52] U.S. Cl. .......................... 600/201; 600/204; 600/210
[58] Field of Search .................................. 600/235, 315, 600/216, 214, 227, 201, 210, 204

[56] References Cited

U.S. PATENT DOCUMENTS

| | | | |
|---|---|---|---|
| 3,724,449 | 4/1973 | Gauthier ................................... | 600/315 |
| 5,245,987 | 9/1993 | Redmond et al. ......................... | 128/20 |
| 5,271,385 | 12/1993 | Bailey ....................................... | 128/20 |
| 5,318,012 | 6/1994 | Wilk ......................................... | 600/235 |
| 5,372,147 | 12/1994 | Lathrop et al. ........................... | 128/898 |
| 5,375,591 | 12/1994 | Mouret ...................................... | 128/20 |
| 5,390,664 | 2/1995 | Redmond et al. ......................... | 128/20 |
| 5,474,056 | 12/1995 | Laboric et al. ........................... | 600/214 |
| 5,580,344 | 12/1996 | Hasson ..................................... | 600/216 |
| 5,613,939 | 3/1997 | Failla ....................................... | 600/601 |
| 5,667,481 | 9/1997 | Villalta et al. ........................... | 600/227 |

OTHER PUBLICATIONS

Gasless Laparoscopy with mechanical peritoneal distention—"Origin"–1993—Eli Lilly And Company.
"Gasless laparoscopy–useless of useful?"—Dr. Daid J. Hill, Dr. Peter J. Maher and Dr. E. Carl Wood –The journal of the American Association of Gynecologic Laparoscopists, vol. 1, No. 3, May 1994, pp. 265–268.

*Primary Examiner*—Jerome Donnelly
*Attorney, Agent, or Firm*—Abelman, Frayne & Schwab

[57] ABSTRACT

A laparoscopic elevator to simultaneously lift the four quadrants of an abdominal cavity for laparoscopic surgery, comprising al least a lifting member for each quadrant, each of which is individually introduced into the abdominal cavity of a patient and including; a horizontal lifting portion in order to lift the abdominal wall of a the abdominal cavity of the patient; a vertical flat holding portion, at approximately 90° regarding the horizontal portion; and an elbow portion which has an angular torsion to place the horizontal portion oriented towards one of the quadrants regarding the vertical portion of the first lifting member; and a holding handle which receives and holds each of the vertical portions of the lifting members.

26 Claims, 8 Drawing Sheets

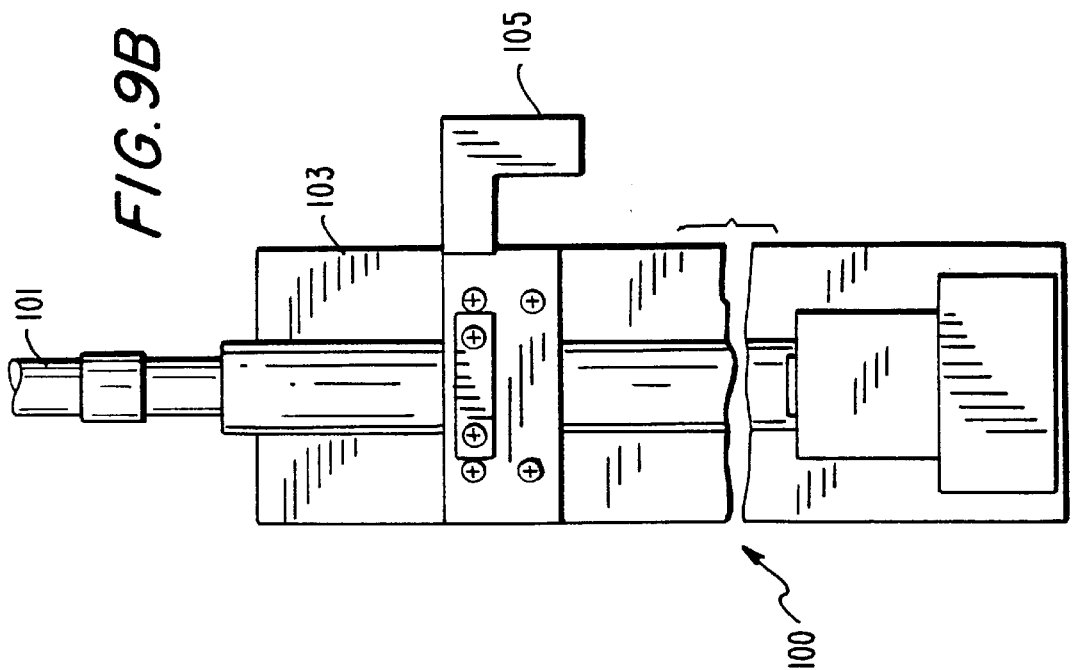
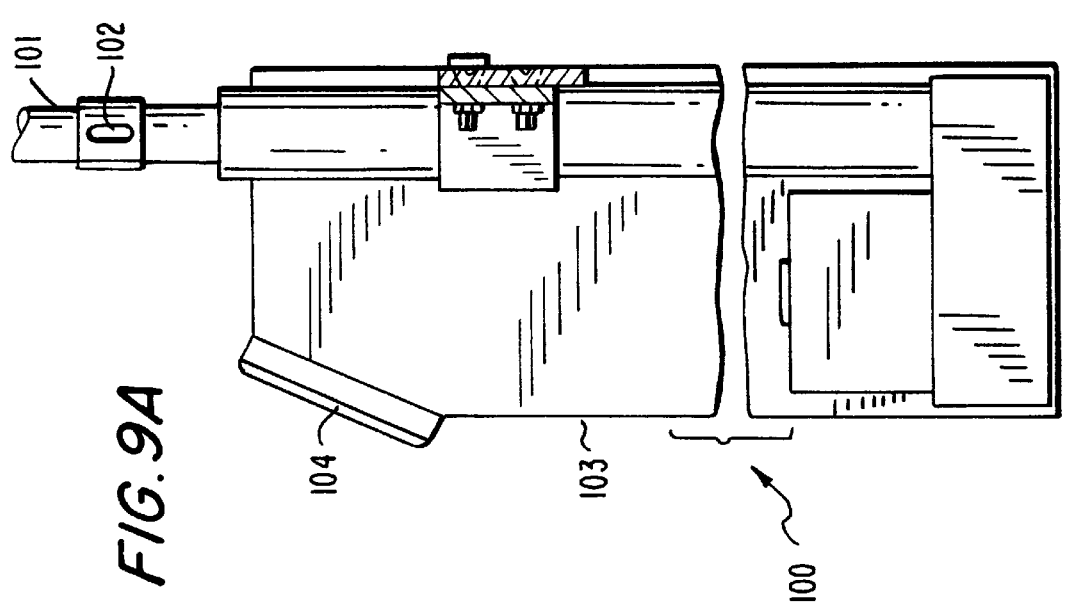

LAPAROSCOPIC ELEVATOR TO SIMULTANEOUSLY LIFT THE FOUR QUADRANTS OF AN ABDOMINAL CAVITY FOR LAPAROSCOPIC SURGERY

BACKGROUND OF THE INVENTION

A. Field of the Invention

The present invention relates to a laparoscopic elevator to lift the abdominal cavity of a patient during laparoscopic surgery without gas, and more particularly, to a laparoscopic elevator to simultaneously lift the four quadrants of an abdominal cavity to perform laparoscopic surgery.

B. Description of the Related Art

Laparoscopic surgery has been greatly developed during the last decade mainly due to the fact that surgery is performed through minimal incisions, so that pain suffered by the patient and the postoperative recovery period considerably reduced, with the subsequent saving in disability time and suffering.

To perform this type of surgery it is required to make a space in the abdominal cavity of the patient in order to introduce both the optical catheter and the surgical instruments, in such a manner that it allows the separation of the organs and optical instruments from the visceral area to be treated and, at the same time, make the surgical tasks easier.

In the conventional laparoscopic surgery, the above referred abdominal space is achieved by inflating the abdominal cavity with gas under pressure, normally carbon dioxide, using very sophisticated and expensive apparatuses.

Such a technique presents anesthetic and physiological risks which may be mortal in nature. Serious and mortal damages have also been reported with the blind introduction of needles and surgical instruments, since they may cause an injury of the intestines and large pelvic vessels.

Laparoscopic surgery aided with the inflating gas also presents some inconveniences and important technical surgical difficulties, such as the fact that requires specialized instruments which are very expensive and difficult to handle since they have to be introduced through sleeves or tubular handles with valves including elements to maintain hermetic conditions in order to prevent the escape of the gas, and the instruments have to be adapted to the gauge of said sleeves. Furthermore, it is required that the sewing needles be straight to be introduced through the sleeves or handles, making their use difficult and defective.

Additionally, because of the characteristics of the instruments which are used, these are usually of the disposable type since they cannot be sterilized to be used in other patients.

Other instruments proposed to be used in laparoscopic surgery are described in U.S. Pat. Nos. 5,245,967, 5,390,644, and 5,271,385. Such instruments include straight flexible blades, held into a sleeve, normally for performing laparoscopic surgery with the aid of gas, whose unique function is to aid in the separation and holding of the intestines or organs, in order to "move them aside" during the surgery, but they are not suitable to lift the abdominal cavity.

A solution proposed to substitute the use of gas for making a space in the abdominal cavity for laparosocopic surgery, is to provide a hook, known as the "Maher Elevator" which is introduced through two small incisions made on the abdominal cavity, which is simply retained with a chain or string which goes to a pulley fixed onto the roof or onto an elevated position, in order to lift the abdomen, thus forming the needed interior space, such as is mentioned in the Article "Gasless Laparoscopy ¿Useless or Useful?" published by David J. Hill, Peter J. Maher, and E. Carl Wood in the magazine The Journal of the American Association of Gynecological Laparoscopists, Volume 1, No. 3, dated May 3, 1994.

This hook provides an insufficient distention, since it is only introduced into a small length of the hemi-abdomen to be operated, and thus produces a limited space with a "utent-like" effect, insufficient for intestinal manipulation, instead of an ample space that is necessary to obtain a good visualization of the area to be operated.

Lastly, the most important advance to make a space enough in the abdominal cavity for performing laparoscopic surgery is represented by the apparatus developed by the company Origin Medsystems of Menlo Park, Calif., USA, named "Laparolift", cited in the previously mentioned publication and published in its pamphlet, that consists of two blades of diverse forms that are fixed to a holding element of an electro-mechanical elevating apparatus, and which are introduced into the abdominal cavity to lift one of the quadrants corresponding to that pair of blades, i.e., there is a pair of adapted blades to lift only one of the four quadrants.

Although such apparatus can be used to provide a space for laparoscopic surgery instead of using gas, it still has the disadvantage that requires a pair of blades to lift only one quadrant of the abdominal cavity, at the same time, providing again the "tent-like" effect which has as a result that the intestines and internal organs move filling the cavity made, thus making the surgery difficult. In addition, the blades of said apparatus are made of disposable materials and they cannot be sterilized. And last but not least, the arm that holds said apparatus cannot be sterilized because of its characteristics and for that reason it has to be covered with sleeves or plastic bags which are very poor regarding to their "sterile" requirements.

Concluding, for the laparoscopic surgery, it is absolutely necessary to provide an ample and enough space or cavity so that it is not invaded or filled with the patient's intestines or organs.

The laparoscopic elevator herein described provides such an ample abdominal space, cavity or distention, in a mechanical way, enough to perform the laparoscopic surgery with great efficiency and economy, allowing the use of the surgical instruments used in a conventional open abdominal surgery such as pliers, scissors, needle holders, sutures, etc., which provide great firmness and safety, eliminating the use of gas under pressure with all of the previously described inherent dangers, and avoiding the use of special and expensive surgical instruments and sleeves with valves to avoid deflation and preventing dangerous blind abdominal punctures.

The inventive concept of the present invention resides in providing a laparoscopic elevator to simultaneously lift the four quadrants of an abdominal cavity for laparoscopic surgery, having a cupola effect which provides an adequate visual space and room for intestinal mobilization and contention, which includes at least one lifting member for each quadrant, each of which is individually introduced in the abdominal cavity of a patient, and including: a horizontal lifting portion to lift the abdominal wall of a patient; a vertical flat holding portion at approximately 90 regarding the horizontal portion; and an elbow portion having an angular torsion to place the horizontal portion oriented towards one of the quadrants in respect to the horizontal portion of the first lifting member; and a holding handle that receives and holds each of the vertical portions of the lifting members and that is adapted to be coupled to an independent transmission arm that in turn is coupled to an electromechanical lifting apparatus. Such lifting apparatus is held to a suitable side of the operating table for lifting or lowering the abdominal cavity of a patient.

In addition to the advantages above described, this laparoscopic elevator has the additional advantage that, when the lifting members are introduced, one by one into the abdominal cavity of a patient, the optical catheter can be introduced with the first one, in order to observe the location of the first and subsequent introduced lifting members within the abdominal cavity, taking care that none internal organ whatsoever be squeezed, strangled or damaged, and simultaneously lift the four quadrants without having the "tent-like" effect, thus providing a sufficient and adequate space for performing surgery.

Also, because of the structure of the lifting members, of the handle and of the retaining arm, these can be manufactured from materials that can be sterilized (for example, stainless steel), and also those components which will be introduced into the patient, and everything that is used in the operative field, can be sterilized with gas, liquid or in an autoclave, without the need of using sleeves or plastic bags.

The contact surface of the five lifting members and their shape, increase the contact area with the abdominal peritoneum, which reduces the possibilities of a lesion by compression.

Due to the reduced gauge of the apparatus which is introduced into the patient, the sub-umbilical microlaparotomy can be of a reduced size.

SUMMARY OF THE INVENTION

It is therefore a main objective of the present invention to provide a laparoscopic elevator to simultaneously lift the four quadrants of an abdominal cavity to perform laparoscopic surgery.

It is also a main objective of the present invention, to provide a laparoscopic elevator to simultaneously lift the four quadrants of an abdominal cavity to perform laparoscopic surgery, of the nature previously disclosed, with which a cupola effect is obtained providing a suitable visual space and room for intestinal mobilization and contention, to perform laparoscopic surgery.

It is another main objective of the present invention, to provide a laparoscopic elevator to simultaneously lift the four quadrants of an abdominal cavity to perform laparoscopic surgery, of the nature previously mentioned, through which, due to the contact surface and shape of its lifting members, an increase of the contact area with the abdominal peritoneum is attained, thus reducing the possibilities of a lesion by compression.

It is still another objective of the present invention, to provide a laparoscopic elevator to simultaneously lift the four quadrants of an abdominal cavity, to perform laparoscopic surgery, of the above mentioned nature, which has the following advantages over the known previous elevators:

A. Safety: The installation of the elements of this apparatus to cause the abdominal distention and the introduction of the surgical instruments, is carried out under direct vision through a sub-umbilical microlaparotomy of 2.5 cm., thus preventing blind punctures as well as the anesthetic and physiological risks of the gas under pressure.

B. Use of conventional Instruments: Surgical instruments commonly used in conventional open surgery, which are stronger, safe and efficient, can be used with the apparatus of the present invention. The use of curved needles for suturing is also possible. These instruments do not exclude, whatsoever, the use of specialized laparoscopic instruments in case that these provide any circumstantial advantage.

C. Economy: The use of expensive abdominal insufflation apparatuses, specialized instruments, and surgical instruments with valves, which can be delicate and not very efficient, is avoided. Furthermore, the constant replacement of such instruments, many of which are manufactured of disposable materials, is also avoided.

D. Time of Operation: It can be reduced because of the fact that the instruments used are more efficient and easy to handle.

E. Due to the reduced gauge of the apparatus of the present invention, which is introduced into the patient, the sub-umbilical microlaparotomy can also be of a smaller size.

F. The components of the apparatus of the present invention, which are introduced into the patient, and everything that is used in the operation field, can be manufactured of a material that can be sterilized with gas, liquid or in an autoclave.

It is an additional objective of the present invention, to provide a method for assembling and introducing the laparoscopic elevator into the abdominal cavity of a patient, to simultaneously lift the four quadrants of an abdominal cavity to perform the laparoscopic surgery, having a cupola effect which provides a suitable visual space and room for intestinal mobilization and contention.

It is a further objective of the present invention, to provide a method for assembling the above disclosed laparoscopic elevator, in which each one of the lifting members of the laparoscopic elevator is introduced in the abdominal cavity of a patient, assembled in a holding handle and held in place to simultaneously lift the four quadrants of the abdominal cavity to perform the laparoscopic surgery.

These and other objectives and advantages of the laparoscopic elevator of the present invention and its method of assembling and using it, will become apparent to those persons having an ordinary skill in the field, from the following detailed description of the invention which will be made with reference to the accompanying drawings.

BRIEF DESCRIPTION OF THE DRAWINGS

FIGS. 9a and 9b, are lateral and rear elevation views of the lifting apparatus which is used in combination with the laparoscopic elevator of the present invention.

DESCRIPTION OF THE SPECIFIC EMBODIMENTS OF THE INVENTION

The invention will now be described referring to the specific embodiments of the same, shown in the attached drawings, wherein the same symbols refer to the same parts of the shown Figures and firstly making reference to its more ample concept, and thereafter specifying the embodiments which the inventor has considered to be the preferred forms that are more suitable to carry out the invention.

Figure 1:
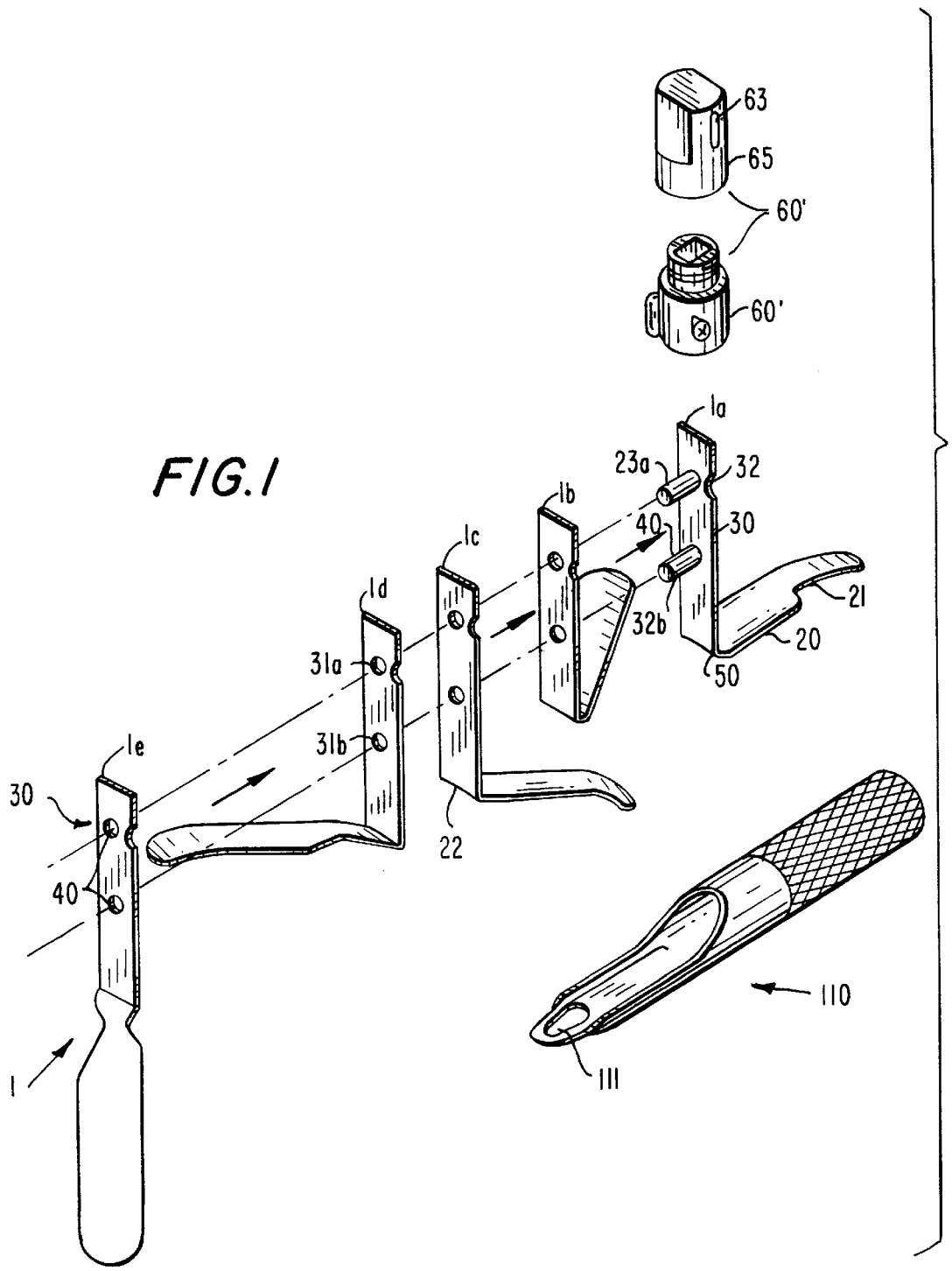
FIG. 1 is an exploded perspective conventional view of the laparoscopic elevator of the present invention, useful to lift the four quadrants of an abdominal cavity to perform laparoscopic surgery, including an embodiment represented by a handle for providing provisional holding, in a position to be assembled and mounted on an electro-mechanical apparatus to lift or lower the laparoscopic elevator.

Referring to FIGS. 1 to 9 of the drawings, the laparoscopic elevator for lifting the four quadrants of an abdominal cavity for effecting laparoscopic surgery, of the present invention, includes:

a) at least a lifting member 1, per quadrant-i.e., the elevator may comprise at least four and preferably five members, 1a, 1b, 1c, 1d, and 1e, (which, for ease of illustration and interpretation, only one will be described, under the understanding that the other members include elements that are common to the first one described)-that may be made of a rigid material, preferably of stainless steel, each of which is able to be individually introduced in the abdominal cavity of a patient and includes:

a horizontal lifting portion 20, to lift the abdominal wall of a patient, which can be of a circular cross section, in the shape of a finger, but which is preferably flat as is illustrated in FIG. 1, whose cross section is slightly curved downward, with rounded edges and corners in order to prevent cutting edges and which is also longitudinally curved downward in order to prevent straight edges that might damage internal tissues, so as to provide a space in the form of a cupola for facilitating surgery;

a vertical flat portion 30, at approximately 90° regarding the horizontal portion 20, which has holding elements 40, to be coupled to the other vertical portions, one after the other; and an elbow portion 50, which has an angular torsion in order to place the horizontal portion 20 oriented towards one of the quadrants regarding to the horizontal portion of the first lifting member-i.e., the elbow portion 50 has a torsion angle in such a manner that each of the horizontal portions 20 are located at approximately 90° to each other;

b) a holding handle 60, preferable made of stainless steel, which has holding elements 70, in order to receive and firmly hold, one after the other, the vertical portions 30, of each of the lifting members 1;

c) a transmission arm 80, preferably of stainless steel, which has holding elements 90, to which the holding handle 50 together with the vertical portions 30, of the lifting members 1, are fixed and retained; and d) an electro-mechanical lifting apparatus 100, to which the transmission arm 60, is adapted and which has an ascending and descending rod 101, to transmit the ascending and descending movement of this apparatus, which is firmly fixed, preferably, to one of the edges of the operating table.

Figure 2A:
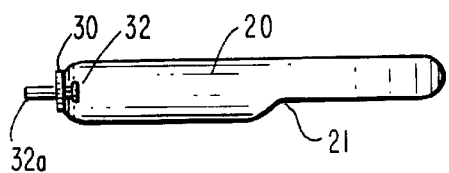
FIGS. 2a, 2b, 2c, and 2d are detailed upper, frontal and lateral elevations, and perspective views, respectively, of one of the lifting members of the laparoscopic elevator of FIG. 1.
Figure 2B:
Figure 2C:
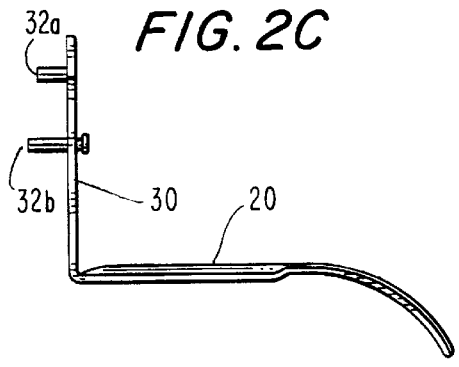
Figure 2D:
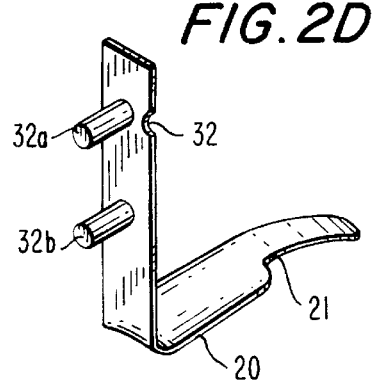

In a preferred embodiment of the laparoscopic elevator of the present invention, each of the lifting members 1a, 1b, 1c, 1d, and 1e, is manufactured from a stainless steel sheet, in the following manner:

First lifting member 1a (FIG. 1 and 2a–2d): this includes a vertical portion 30a of 5.08×1.27×0.31 cm. (2×½×⅛ inches), which continues in an angle of approximately 90° to the horizontal section 20, of approximately 10.16×1.9×0.31 cm. (4×¾×⅛ inches) with a narrowing 21a at 1.27 cm. (½ inch) at its left side; this in order to allow the introduction of an optical catheter (not shown)), and the elbow portion 50 has a torsion angle that places the horizontal portion 20 at a 0°, regarding the first quadrant of the 360°, this blade having a slight longitudinal curvature downward in a cross section view, in order to provide the cupola effect. In a more preferred embodiment, instead of, or in addition to the narrowing 21, the horizontal portion 20a, and if desired, all of the other horizontal portions 20b, 20c, 20d and 20e, present a slight transversal curvature 22, as is shown in FIGS. 1 and 2d, in order to make easy the introduction of the optical catheter.

Holding elements of the lifting members: The holding elements 40, (FIG. 1) of each of the vertical portions 30, may consist in one, and preferably two circular perforations 31a and 31b, having a diameter of about 0.95 cm. (⅜ of an inch) on its flat surface, and a semicircular notch 32, on its right edge, in order to couple and hold all of the lifting members 1, one after the other, in the holding handle 60.

However, in an embodiment of the invention, for the self assembly of the holding members 1, the first of these, i.e. the holding member 1a, can include two pins, 32a and 32b of about 0.95 cm. (⅜ of an inch) in order to be received by the perforations 31a and 31b of the other lifting members, 1.

Second lifting member 1b: (FIG. 1): It includes a vertical portion 30, of approximately 5.14×1.27×0.06 cm. (2 ¹⁄₁₆×½×¹⁄₁₆ of an inch), presenting its two perforations 31a and 31b, to allow the introduction of the holding pins 32a and 32b of the first lifting member 1a, and the notch 32, on its right edge, in order to be held in the holding handle 60; and it continues in a horizontal portion 20b of about 10.16×1.27×0.06 cm (×½×¹⁄₁₆ of an inch) at 90° in a lateral view, and its elbow portion 50, has a torsion angle which places the horizontal portion 20, at 55° regarding the 360° quadrant.

The third lifting member, 1c.: (FIG. 1). It includes a vertical portion 30, of about 5.20×2.27×0.06 cm. (2 ⅛×½×¹⁄₁₆ of an inch), presenting its two perforations 31a and 31b, and its notch 32, on its right edge, and continues in a horizontal portion 20, of 10.16×1.27× 0.06 cm. (4×½×¹⁄₁₆ of an inch), at 90° in a lateral view and its elbow portion 50, has a torsion angle which places the horizontal portion 20c at 125° regarding the 360° quadrant.

The fourth lifting member, 1d: (FIG. 1). It includes a vertical portion 30, of 5.14×1.27×0.06 cm (2 ¹⁄₁₆×½× 1716 of an inch), presenting its two perforations 31a and 31*b*, and its notch 32, on its right edge, and continues in a horizontal portion 20, of 10.16×1.27× 0.06 cm (4×½×⅟16 of an inch), at 90° in a lateral view and its elbow portion 40 has a torsion angle which places the horizontal portion 20, at 235° regarding the 360° quadrant.

The fifth lifting member, 1*e* (FIG. 3) comprising a vertical portion 30, of 5.20×2.27×0.06 cm (2 ⅛×½×⅟16 inches), presenting its two perforations 31*a* and 31*b*, and its notch 32 on its right edge, and continues in a horizontal portion 20, of 10.16×1.27×0.06 cm (4×½×⅟16 of an inch), at 90° in a lateral view and its elbow portion 50, has a torsion angle which places the horizontal portion 20*e*, at 325° regarding the 360° quadrant.

Figure 6:
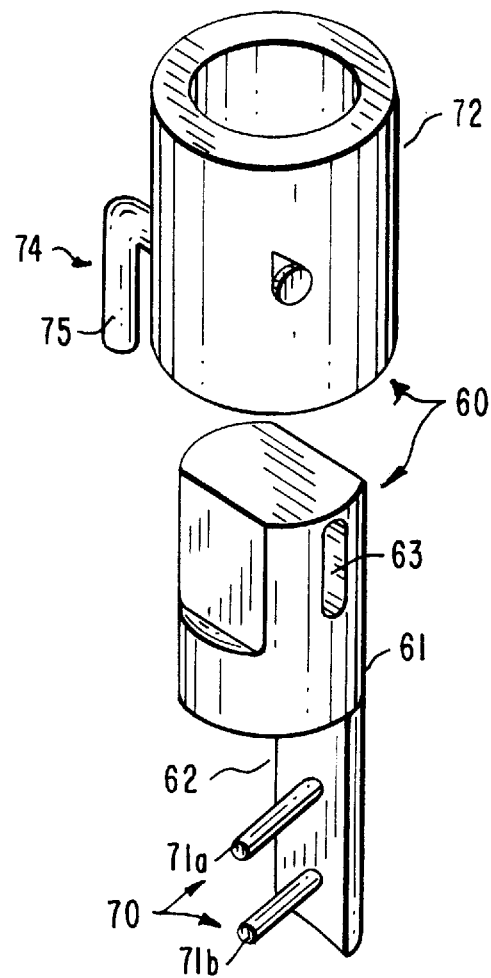
FIG. 6 is an exploded conventional perspective view of another embodiment of the holding handle of the laparoscopic elevator of FIG. 1.
Figure 7:
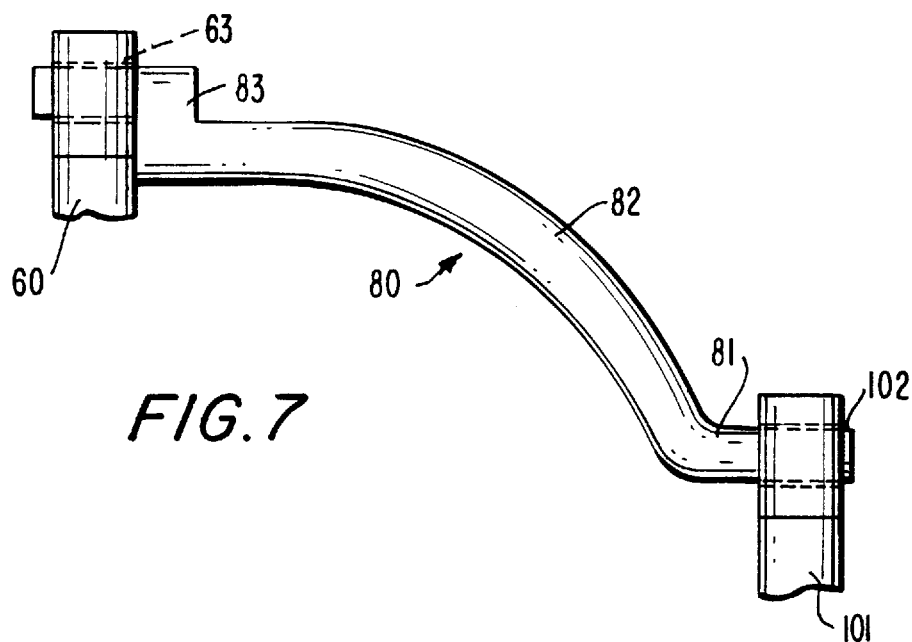
FIG. 7, is a lateral elevation view of an embodiment of the transmission arm of the laparoscopic elevator of the present invention.
Figure 8:
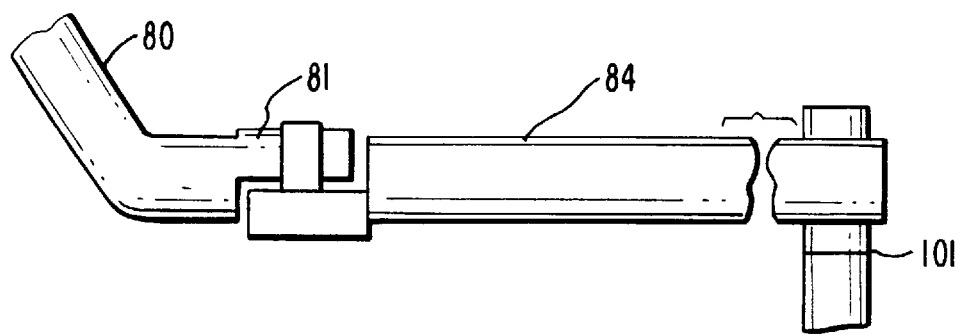
FIG. 8, is a partial elevation lateral view of a second embodiment of the transmission arm of FIG. 7, with an articulated section.

In a first embodiment of the holding handle 60, shown in FIG. 6, this may consist in a cylindrical handle 61 having a lower cross cut 62, and its holding elements include a pair of pins 71*a*, 71*b*, which are included instead of the pins 32*a* and 32*b* of the vertical portion 30*a* of the first lifting member 1*a*, in order to receive the circular perforations 31*a* and 31*b* of all the vertical portions 30 of the lifting members 1, and a ring 72 that is sliding in the cylindrical handle 61, to be placed in a first position upward of the lower cross cut 62, in order to allow the reception of the vertical portions 30, and be slided to a second position covering the cross cut 62 to hold in the vertical portions 30. This ring 72, preferably including a tangential perforation 73, to receive a fastening locking bolt 74. This locking bolt 74 consists of a cylindrical bar, folded at 90°, which shows a first lever portion 75 outside of the ring 72 and a half cane portion 76 (which is better showed in FIGS. 4*c*–4*e*) which is introduced in the tangential perforation 73. So that, in a first position of the half cane portion 76 it is allowed to slide the ring 72 in the handle 60 and cover the vertical portions 30 of the lifting members 1 and in a second position coinciding with the semicircular notches 32 of the vertical portions 30, it is allowed to insert the semicylindrical portion, which is not notched, of the half cane portion 76, in order to retain together, firmly and aligned, the vertical portions 30 of the lifting members 1, one on the other, fixedly maintaining its positions, preventing that said lifting members 1 can rotate or be displaced from the ring 72.

The cylindrical handle 61 has a slot 63 to be telescopically coupled to the transmission arm 80, which is also coupled to the elevator apparatus 100, which imparts upward and downward movements to automatically lift or lower the abdominal cavity of a patient during the laparoscopic surgery.

For the assembling of the laparoscopic elevator of the present invention, is possible to employ a provisional assembly handle 110, of any suitable form, which could be retired once the lifting members 1 have been introduced in the abdominal cavity of a patient, and which comprises an orifice 111 having two diameters, similar to a "lock eye", in order to receive and retain an immediate portion of the head of one of the pins 32*b* of the first vertical portion 30*a* of the first lifting member 1*a*, in order to couple each of the lifting members 1, which are introduced, one by one, in the abdominal cavity of the patient.

Figure 3:
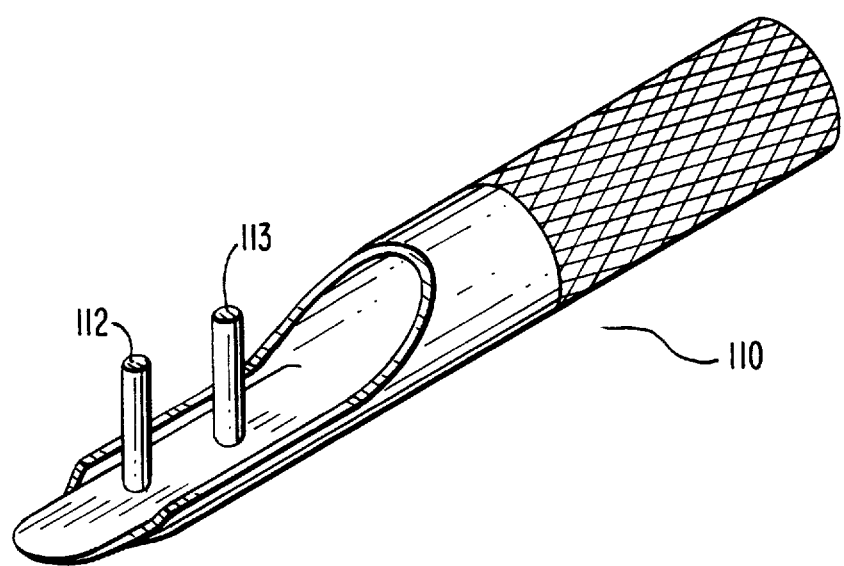
FIG. 3 is conventional perspective view of another embodiment of the provisional holding handle of the laparoscopic elevator of FIG. 1.
Figure 4A:
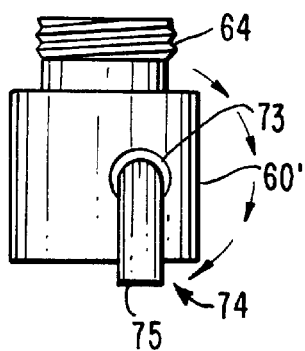
FIGS. 4a, 4b, 4c, 4d, and 4e are detailed frontal elevation, perspective views, two lower plant views in a partial cross section and an upper plant view, respectively, of an embodiment of the holding handle of the laparoscopic elevator of FIG. 1.
Figure 4B:
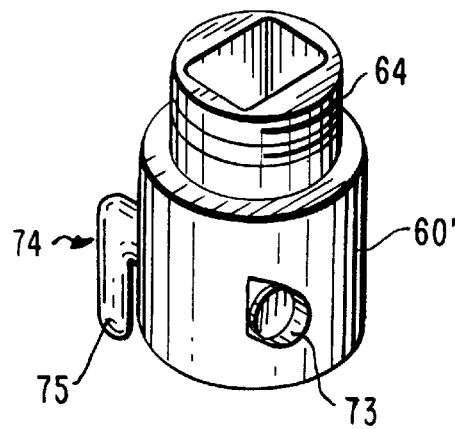
Figure 4C:
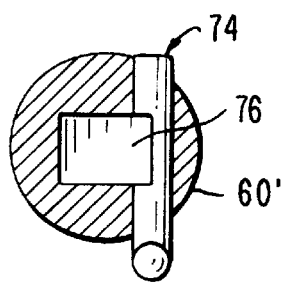
Figure 4D:
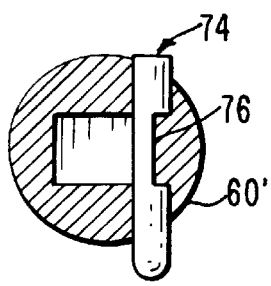
Figure 4E:
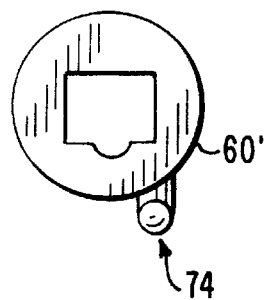
Figure 5A:
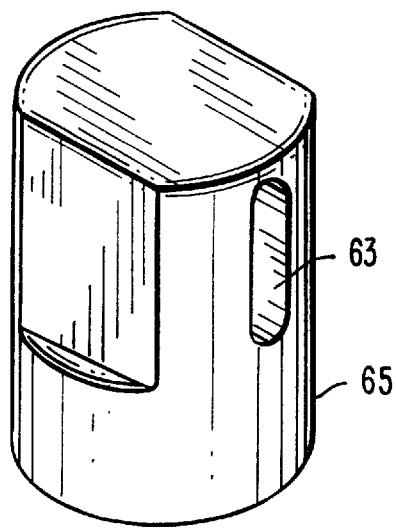
FIGS. 5a, 5b, 5c and 5d are conventional perspective, upper plant, front and lateral views, of an embodiment of a threaded holder for the holding handle of Figures and 4a, 4b, 4c, 4d, and 4e.
Figure 5B:
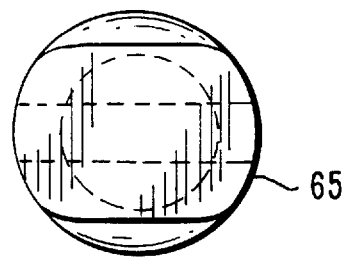
Figure 5C:
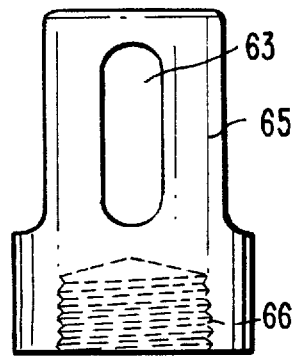
Figure 5D:
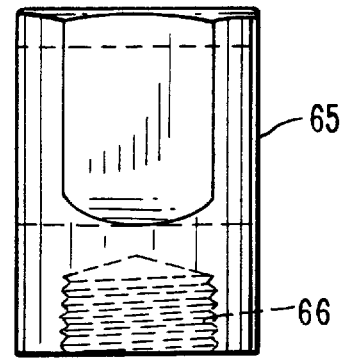

In another embodiment of the provisional handle 110, shown in FIG. 3, this comprises pins 112 and 113 instead of the pins 32*a* and 32*b* of the vertical portion 30*a* of the first lifting member 1*a*, in order to receive each of the vertical portions 30 of the lifting members 1, which are introduced, one by one, in the abdominal cavity of the patient. Said handle 110 is retired from the vertical portions 30, once the horizontal portions 20 have been introduced in the abdominal cavity of a patient, to be retained by the holding handle 60.

A second embodiment of the holding handle 60 (FIG. 1), for the case in which the vertical portions 30 include the pins 32*a* and 32*b*, or else, in case that the provisional handle 110 be used, this may consist only of a tubular member 60' (FIGS. 4*a*–4*e*), including a locking bolt 74 to retain together the vertical portions 30. The tubular member 60' may include an upper slot 62 (not showed in the FIGS. 4*a*–4*e*), to be telescopically coupled to the transmission arm 80 and, notwithstanding of its weight and the dimensions of the components and of the coupling slot, these elements remain duly coupled and inseparable. As a safety step, the handle can include a perforation with a thumbscrew (not showed) which is directed toward the slot 62, in order to fixedly retain the transmission arm 80, once its distance has been adjusted.

The holding handle 60', can include an upper external threaded section 64 to be thread coupled within the carrier 65 (FIGS. 5*a*–5*d*) which has an internal thread 66 and the slot 63 to be telescopically coupled to the transmission arm 80 which in turn will be coupled to the elevator apparatus, so that the slot can be oriented toward the transmission arm 80, without the necessity to rotate all the apparatus.

On the other hand, the transmission arm 80 (FIG. 7) comprises a bar or arm having a straight section 81 to be coupled to the slot 102 of the elevator apparatus 100, a curved section 82 to be adapted to the curvature of the abdominal trunk of a patient allowing a better movement to the laparoscopic apparatus, and a straight section 83 that is telescopically inserted to the slot 63 of the holding handle 60 or of the holder 65.

This transmission arm 80 can also include a fastening section 84 (FIG. 8) coupled articulated to the straight section 83, which is tellescopically coupled to the holding handle 60, in order to allow a lateral movement.

Finally, notwithstanding that the elevator apparatus 100 can be of any suitable type as those existing in the market, preferably this should include an electro-mechanical actuator with a rod 101 having a slot 102 in which the straight portion 81 of the arm 80 is introduced, in order to transmit the upward and downward movements to the laparoscopic elevator of the present invention, as well as, a source of power source and a controller for controlling the actuator. This source of power preferably works with a direct current of 24 volts, with a maximum consumption of 2.75 amperes and with an input of alternating current of 120 volts to 60 hertz; and a metallic protecting cabinet 103 presenting a dial 104 for manual control, which can be handled by remote control and as an option, with a protected foot lever; and a fastening system 105 to be attached to the working table; preferably the actuator and the cabinet are fixed by means of two clamps held to a piece of stainless steel in a "L" shape, designed to be assembled on a track that is fixed to the lateral rail of the operation table.

The method to assembly and use the laparoscopic elevator of the present invention generally comprises the following steps:

introducing the first lifting member and the optical catheter of the laparoscopic apparatus through of a microincision in the abdominal cavity of the patient;

retaining the first lifting member, by means of a holding handle, under a direct vision of the laparoscopic apparatus, taking care that none organ or intestine of the patient could be squeezed, strangled or cut;

sequentially introducing the remainder self-positioning lifting members through of the microincision, again under the direct vision of the laparoscopic apparatus, taking care that none organ or intestine of the patient might be squeezed, strangled or cut and retaining said lifting members my means of the handle;

retaining the transmission arm on an elevator apparatus in order to impart its upward or downward movements;

retaining the holding handle on the transmission arm; and, driving an actuator of the elevator apparatus, to lift or lower the internal space of the abdominal cavity of the patient.

In an specific embodiment of realization, the method of assembly and use of the laparoscopic elevator of the present invention comprising the following steps:

a) practicing a sub-umbilical microlaparotomy of 2 to 2.5 cm. with penetration of peritoneum cavity under direct visualization with the optical catheter;

b) introducing the first lifting member 1a through of the microincision, holding its vertical portion 30 by means of the handle 60 or by the provisional handle 110 in a reference position of 0°;

c) manually elevating the first lifting member 1a, introducing the optical catheter, producing a space in the abdominal cavity, so that the introduction can be examined under direct visualization through of the laparoscopic camera and monitor;

d) sequentially introducing the second, third, fourth and fifth lifting members, which will be assembled to each other, mounting and retaining them in the pins 71a, 71b of the handle 60, in the pins 32a and 32b of the first lifting member 1a, or in the pins 112 and 113 retained by the provisional handle 110, taking care that none organ or intestine of the patient be squeezed, strangled or cut;

e) lowering the ring 72 of the handle 60 in order to cover the vertical portions 30 which are retained by the pins 71a and 71b and lowering the lever portion 75 of the locking bolt 75 to firmly and fixedly retain the vertical portions 30 of the lifting members 1, or else, releasing the vertical portions that are being fastened by the pins 32a, 32b of the first lifting portion 30a of the first lifting member 1a, of the provisional handle 110 which is detachable, in order to be attached on the handle 60';

retaining the transmission arm 80 by means of the elevator apparatus 100, retaining the straight portion 81 of the arm 80 in the fastening system of said apparatus 100;

f) retaining the handle 60 or 60' on the transmission arm 80 which is held by the elevator apparatus 100, inserting the slot 62 of said handle 60 or 60' in the transmission arm 80 and holding it fixedly through of the thumbscrew 64; and g) driving the actuator of the elevator apparatus 100, for simultaneously lift the four quadrants of the abdominal cavity of the patient, to obtain an enough space in a cupola shape, which provide an adequate visual space for performing the laparoscopic surgery.

Finally it must be clear that the laparoscopic elevator, as well as its assembling and using method are not limited exclusively to the above disclosed and illustrated embodiments and that the persons skilled in the field will be able to make modifications to the design and distribution of the components of the laparoscopic elevator and to the steps of the method of the present invention, in accordance with the teaching provided by the invention, which clearly will be within of the true inventive concept and scope of the invention which is claimed in the following claims:

I CLAIM:

1. A laparoscopic elevator to simultaneously lift the four quadrants of an abdominal cavity for laparoscopic surgery, comprising:

at least a first, a second, a third and a fourth lifting members, each including a vertical flat holding portion and a horizontal lifting portion at about 90° regarding the vertical flat holding portion; the horizontal lifting portion of the first lifting member is oriented forward at 90° regarding the vertical flat holding portion; the horizontal lifting portion of the second lifting member having a torsion angle regarding the vertical flat portion of about 90° oriented to the right; the horizontal lifting portion of the third lifting member is oriented backward at 90° regarding the vertical flat holding portion; and the horizontal lifting portion of the fourth lifting member having a torsion angle regarding the vertical flat holding portion of about 90° oriented to the left, whereby each of the horizontal lifting portions of each lifting members is placed at about 90° from each other; and at about 90° regarding the flat vertical holding portion; and holding means receiving and holding each of the vertical flat portions of the lifting members one over the other.

2. The laparoscopic elevator as claimed in claim 1 wherein the horizontal lifting portion of each of the lifting members is curved downward.

3. The laparoscopic elevator as claimed in claim 1 wherein the horizontal lifting portion of each of the lifting members is cylindrical.

4. The laparoscopic elevator as claimed in claim 1 wherein the horizontal lifting portion of each of the lifting members is flat.

5. The laparoscopic elevator as claimed in claim 1 wherein the horizontal lifting portion of each of the lifting members is flat and having rounded corners.

6. The laparoscopic elevator as claimed in claim 1 wherein the horizontal lifting portion of each of the lifting members is convex in cross section.

7. The laparoscopic elevator as claimed in claim 1 wherein the horizontal lifting portion of the first lifting member having a narrowing portion in order to allow the passage of the optical catheter.

8. The laparoscopic elevator as claimed in claim 1 wherein the horizontal lifting portion of the first lifting member having a slot portion to allow the passage of the optical catheter.

9. The laparoscopic elevator as claimed in claim 1 wherein the vertical flat holding portion of each of the lifting members includes fastening means.

10. The laparoscopic elevator as claimed in claim 1 wherein the vertical flat holding portion of each of the lifting members includes fastening means comprising at least a perforation to be attached to the holding means.

11. The laparoscopic elevator as claimed in claim 1 wherein the vertical flat holding portion of each of the lifting members includes fastening means comprising two perforations to be attached to the holding means.

12. The laparoscopic elevator as claimed in claim 1 wherein the vertical flat holding portion of each of the lifting members including fastening means comprising two pins at the vertical flat portion of the first lifting member and two perforations in the vertical flat portion of the second, third and fourth lifting members, to be attached to the holding means.

13. The laparoscopic elevator as claimed in claim 1 wherein the vertical flat holding portion of each of the lifting members including fastening means comprising at least a holding notch at an edge of each of the vertical flat holding portion of the lifting members, to be firmly held together one over the other by the holding means, maintaining the positions of the horizontal lifting portions, at 0°, 90°, 180° and 270°.

14. The laparoscopic elevator as claimed in claim 1 wherein the holding means comprising a holding handle having fastening means for fastening and retaining the fastening means of the vertical flat holding portions, one over the other, maintaining the positions of the horizontal lifting portions at 0°, 90°, 180° and 270°.

15. The laparoscopic elevator as claimed in claim 1 wherein the holding means comprising a tubular holding handle in order to internally receive the vertical flat holding portions of the lifting members and also includes fastening means for internally fastening and retaining the vertical flat holding portions of the lifting members one over the other, maintaining the positions of the horizontal lifting portions at 0°, 90°, 180° and 270°.

16. The laparoscopic elevator as claimed in claim 1 wherein the holding means comprising a tubular holding handle having a holding locking bolt to retain the vertical flat holding portions of the lifting members, one over the other, maintaining the positions of the horizontal lifting portions, at 0°, 90°, 180° and 270°.

17. . The laparoscopic elevator as claimed in claim 1 wherein the holding means comprising a tubular holding handle having a holding locking bolt consisting in a cylindrical bar bent at about 90° presenting a cylindrical locking section having a longitudinal flat cutoff portion presenting a flat portion and a semicylindrical portion and is introduced tangentially into the handle, and a lever section located outside of the handle, so that, in a first position of the lever portion, the flat portion of the locking section allows the passage the vertical flat holding portions of the lifting members into the holding handle and, in a second position of the lever section allows the introduction of the semicylindrical portion into the notches of the vertical flat holding portions in order to retain the vertical flat holding portions of the lifting members together, one over the other, maintaining the positions of the horizontal lifting portions at 0°, 90°, 180° and 270°.

18. The laparoscopic elevator as claimed in claim 1 wherein the holding handle comprising a cylindrical bar having a longitudinal flat cutoff portion at a lower end, presenting a flat portion and a semicylidrical portion; fastening bolts perpendicularly placed at the flat portion of the lower end of the cylindrical bar, lifting members; and a sliding ring to be slide introduced over the cylindrical bar covering the cutoff portion of the cylindrical bar, and comprising the fastening locking bolt to retain the vertical flat holding portions of the lifting members into the sliding ring.

19. The laparoscopic elevator as claimed in claim 1 wherein the holding handle comprising fastening means consisting in an external threaded section at an upper end; an internal threaded carrier to be screwed to the external threaded section of the holding handle, to allow rotary movement of the holding handle.

20. The laparoscopic elevator as claimed in claim 1 wherein the holding handle includes a slot to be coupled to an elevator device.

21. The laparoscopic elevator as claimed in claim 1 wherein the holding handle comprising fastening means comprising an external threaded section at an upper end; and an internal threaded carrier to be screwed to the external threaded section of the holding handle, including a slot to be coupled to an elevator device.

22. The laparoscopic elevator as claimed in claim 1 further comprising a transmission arm to retain the holding handle of the lifting members, to be coupled to an elevator device.

23. The laparoscopic elevator as claimed in claim 1 comprising a transmission arm having a curved section having a first end to be coupled to the holding means and a second end to be coupled to an elevator device.

24. The laparoscopic elevator as claimed in claim 1 comprising a transmission arm having a curved section having a first end to be coupled to the holding means and a second end having an articulated section to be coupled to the elevator device.

25. The laparoscopic elevator as claimed in claim 1 further comprising a provisional assembly handle having pins to be introduced into the perforations of the vertical flat holding portions of each of the lifting members, which is retired once that all of the lifting members have been assembled together.

26. The laparoscopic elevator as claimed in claim 1 comprising a provisional assembly handle compriseing a slot, to receive the pins of the vertical flat holding portion of the first lifting member.

* * * * *